United States Patent

Igwebike

[11] 4,033,338
[45] July 5, 1977

[54] VIBRATORY FEMININE HYGIENE VACUUM DEVICE

[76] Inventor: Kingsley Igwebike, 4152 Somerset Drive, Los Angeles, Calif. 90008

[22] Filed: June 4, 1976

[21] Appl. No.: 692,725

[52] U.S. Cl. .............................. 128/36; 128/276; 128/38

[51] Int. Cl.² .......................................... A61H 1/00

[58] Field of Search .............. 128/34–40, 128/275–278, 230, 2 B

[56] References Cited

UNITED STATES PATENTS

| | | | |
|---|---|---|---|
| 1,048,316 | 12/1912 | Johnson | 128/278 |
| 1,863,930 | 6/1932 | McKesson | 128/278 |
| 3,044,465 | 7/1962 | Anderson et al. | 128/230 |
| 3,078,579 | 2/1963 | Jones et al. | 128/276 X |
| 3,504,665 | 4/1970 | Bakunin et al. | 128/36 |
| 3,517,665 | 6/1970 | Sheldon | 128/276 X |

*Primary Examiner*—Lawrence W. Trapp

[57] ABSTRACT

A feminine hygiene vacuum device includes an elongated flexible tubular intake portion for insertion into the vaginal tract. A motor driven centrifugal impeller within the device creates a radially inward air flow through plural intake ports in the tubular wall of the intake portion. An arm within the intake portion extends radially from a longitudinally directed motor driven rotating shaft and engages the interior wall of the intake portion. The intake portion undergoes a vibratory flexure in response to rotation of the shaft.

2 Claims, 2 Drawing Figures

VIBRATORY FEMININE HYGIENE VACUUM DEVICE

FIELD OF THE INVENTION

The present invention relates generally to vacuum cleaning devices. In its particular aspects, it relates to a device for cleaning the vaginal tract.

BACKGROUND OF THE INVENTION

In the prior art, various liquid douche solutions have been used for cleaning the vaginal tract. These solutions are difficult and time consuming to use. While various vacuum cleaning devices have heretofore been known, none are applicable for cleaning the vaginal tract.

OBJECTS OF THE INVENTION

It is an object of the present invention to provide a vacuum cleaning device having an intake portion proportioned for insertion into the vaginal tract and configured for removing debris from the walls of the vagina.

It is a further object of the present invention to provide a vacuum cleaning device with an elongated flexible intake portion which is vibrated in flexure to aid in cleaning the vaginal tract.

SUMMARY OF THE INVENTION

Briefly, the aforementioned and other objects of the present invention are satisfied by providing a feminine hygiene vacuum device which includes an elongated flexible tubular intake portion having plural spaced apart apertures in its tubular wall for picking up debris from the walls of the vagina. A motor driven impeller creates an air flow including radially inward paths through the intake ports which paths merge into a path directed longitudinally within the intake portion. A collection bag is provided intermediate the latter path.

For vibrating the intake portion in flexure, a longitudinally directed motor driven rotating shaft is provided within the intake portion. An arm or other suitable eccentric extends radially from the shaft and slideably engages the interior wall of the intake portion. The arm is sufficiently long to flex or bend the intake portion in the direction of extension of the arm. As the shaft and arm are rotated, the intake portion undergoes a vibratory or cyclical flexure for loosening the debris on the walls of the vaginal tract.

Other objects, features and advantages of the present invention will become apparent upon perusal of the following detailed description of the preferred embodiment thereof when taken in conjunction with the appended drawing wherein:

FIG. 1 is a pictorial presentation of the feminine hygiene device of the present invention, generally in side elevation; and FIG. 2 is a cross-sectional elevational side view of the device in FIG. 1.

DETAILED DESCRIPTION

Figure 1:
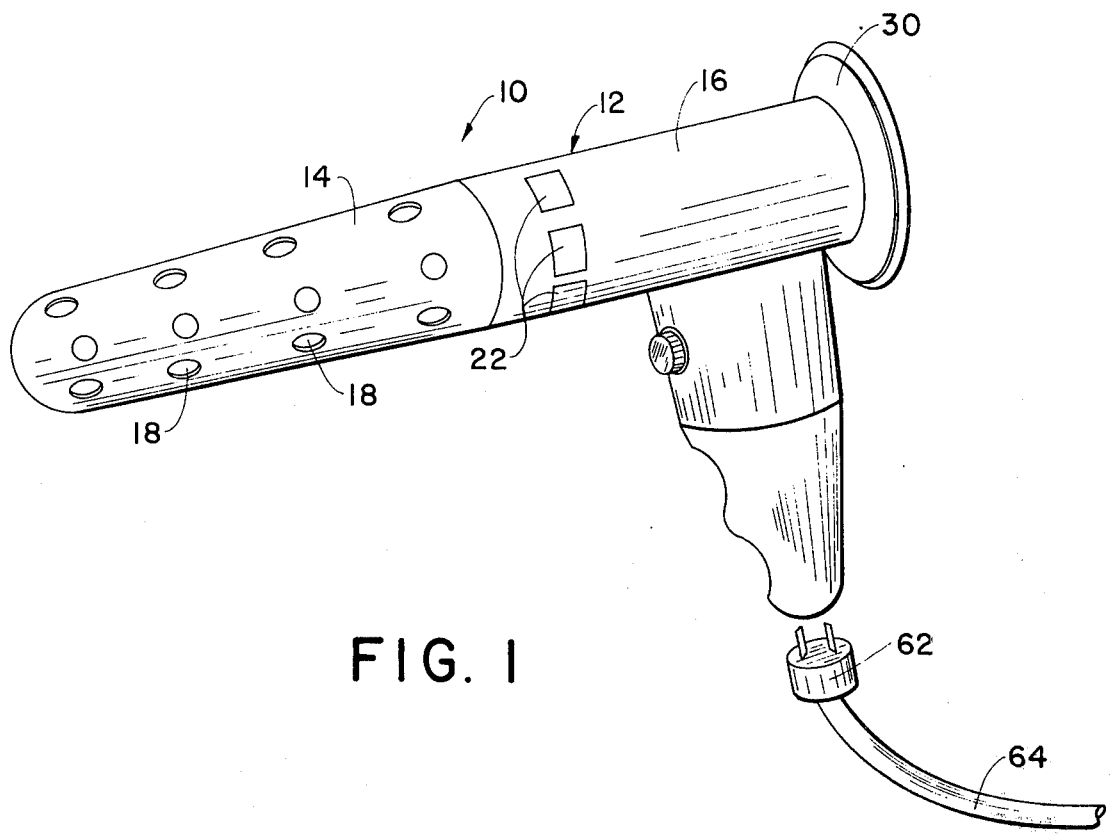
Figure 2:
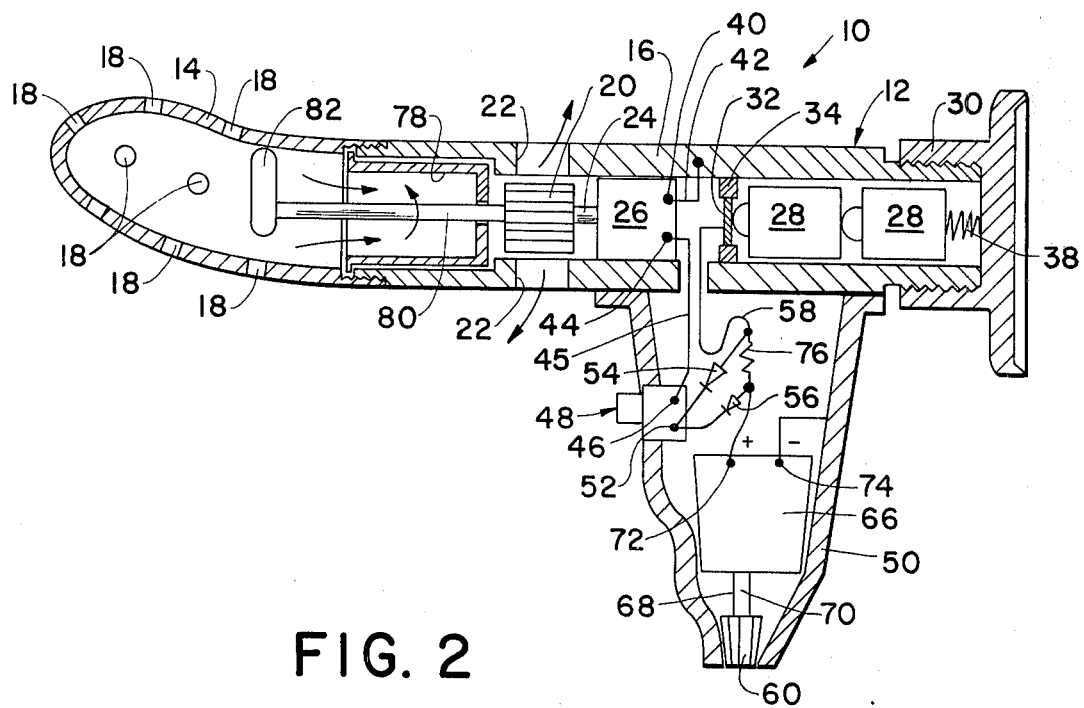

Referring to FIGS. 1 and 2 of the drawing, the feminine hygiene vacuum device of the present invention is generally indicated by the reference numeral 10 and is seen to be generally self-contained in a gun-shaped housing 12. Device 10 includes an elongated flexible tubular intake portion 14, as of rubber, threadably engaged on a metal rear portion 16 of housing 12.

Plural apertures 18 are distributed along the surface of intake portion 14 to serve as generally radially directed intake ports. The intake portion 14 is proportioned to be inserted into the vaginal tract to enable debris from the walls of the tract to be taken into the interior of portion 14 via apertures or ports 18.

In order to provide the requisite suction, a centrifugal fan or impeller 20 is mounted in portion 16 coaxially with intake portion 14. The fan 20 is configured to take in air along its axis and project air outward through plural angularly spaced apart exhaust ducts 22 in housing portion 16 disposed about the circumference of fan 20. Fan 20 is driven by the output shaft 24 of a D.C. motor 26 disposed coaxially behind fan 20.

Disposed coaxially behind motor 26 are a column of batteries 28, which are loadable or removeable via a threaded cap 30 carried on the rear end of housing portion 16. A generally circular contact element 32 carried in a annular ring 34 of dielectric material is positioned proximate motor 26 and contacts a front or positive end of the column of batteries 28. A rear or negative end of the column of batteries 28 is grounded to housing portion 16 via a metal spring 38 acting against the metal cap 30.

One terminal 40 of motor 26 is grounded to housing portion 16 as by a lead 42. The other terminal 44 of motor 26 is coupled via a lead 45 to one terminal 46 of a normally-open push-button trigger switch 48 carried by a hollow metal handle portion 50 of housing portion 16. The other terminal 52 of switch 48 is coupled to the cathodes of a pair of semiconductors diodes 54, 56. The anode of diode 54 is connected to contact 32 via a lead 58.

For accepting 110 Volt A.C. power input a female socket connector 60 is carried at the bottom of handle portion 50 and is adapted to receive a male connector 62 or the end of a power cable 64. The socket 60 feeds an A.C. to D.C. convertor 66 housed within handle portion 50 via leads 68, 70. Convertor 66 is configured to produce a voltage between its positive and negative output terminals 72, 74 which is slightly greater than the voltage of the column of batteries 28. The positive output terminal 72 is connected to the anode of diode 56 and the negative output terminal 74 is grounded. Thus when switch 48 is depressed power is supplied from batteries 28 to motor 26 if the plug 62 is not engaged in socket 60 and is supplied from converter 66 if the plug 62 is engaged in socket 60. For trickle charging the column of batteries 28, from convertor 66, a resistor 76 is connected between the anodes of diodes 54, 56.

It will be appreciated that when motor 26 is energized, the fan 20 produces an intake air path directed radially inward through ports 18 and longitudinally along the interior of intake portion 14. A semi-porus collection bag 78 is removeably retained in the front part of housing portion 16 intermediate the air path for trapping particulate matter while allowing air to pass therethrough to fan 20.

For vibrating the intake portion 14 in flexure to loosen debris from the vaginal tract, a rotary shaft 80 extends longitudinally forward from fan 20, through bag 78, and into the intake portion 14. The shaft 80 is secured fixedly to fan 20 for rotating therewith as a unit. An arm or suitable eccentric cam 82 extends radially and fixedly from the forward end of shaft 80. The free end of arm 82 slideably engages the interior of the wall intake portion 18 and is of a length to flex or bend the intake portion, as shown in FIG. 2, in the direction of the extension of the arm. As the arm 82 is rotated by shaft 80, the intake portion 14 undergoes a vibratory or cyclical flexure.

While the preferred embodiment of the present invention has been described and illustrated in specific detail it should be understood that numerous modifications, additions and omissions in the details thereof are possible within the intended sprit and scope of the invention claimed herein.

What is claimed is:

1. A feminine hygiene vacuum device comprising: a housing including an elongated tubular flexible intake portion for insertion into the vaginal tract; a plurality of spaced-apart intake ports formed in the tubular wall of said intake portion; motor means with said housing; an impeller within said housing driven by said motor means, said impeller being positioned for setting up a path of air flow radially inward through said intake ports and longitudinally along the interior of said intake portion; and a collection bag within said housing intermediate said path of air flow.

2. The device of claim 1 futher comprising a longitudinally directed shaft within said intake portion coupled for being rotated by said motor means; and an arm extending radially and fixedly from said shaft and slideably engaging the interior wall of said intake portion for flexing said intake portion in the direction of extension of said arm whereby said intake portion undergoes vibratory flexure in response to rotation of said shaft.

* * * * *